US009419372B2

(12) United States Patent
Swanson et al.

(10) Patent No.: US 9,419,372 B2
(45) Date of Patent: Aug. 16, 2016

(54) VENTED SET SCREW FOR IMPLANTABLE MEDICAL DEVICE

(75) Inventors: Lawrence D. Swanson, White Bear Lake, MN (US); John M. Edgell, Plymouth, MN (US); Nick A. Youker, River Falls, WI (US); Scott Dahl, Minneapolis, MN (US); Kevin P. Rodby, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1001 days.

(21) Appl. No.: 12/911,086

(22) Filed: Oct. 25, 2010

(65) Prior Publication Data

US 2011/0098763 A1    Apr. 28, 2011

Related U.S. Application Data

(60) Provisional application No. 61/255,373, filed on Oct. 27, 2009.

(51) Int. Cl.
*A61N 1/375* (2006.01)
*H01R 13/52* (2006.01)
*H01R 4/36* (2006.01)

(52) U.S. Cl.
CPC .......... *H01R 13/5227* (2013.01); *A61N 1/3752* (2013.01); *H01R 4/36* (2013.01); *H01R 2201/12* (2013.01); *Y10T 29/49174* (2015.01)

(58) Field of Classification Search
USPC .......................................................... 607/37
See application file for complete search history.

(56) References Cited

U.S. PATENT DOCUMENTS

| 5,593,410 | A | 1/1997 | Vrespa |
| 6,039,685 | A | 3/2000 | Bushek |
| 6,059,786 | A * | 5/2000 | Jackson ........................ 606/916 |
| 7,231,253 | B2 * | 6/2007 | Tidemand et al. .............. 607/37 |
| 7,305,267 | B2 | 12/2007 | Hector |
| 2005/0131481 | A1* | 6/2005 | Ries et al. ....................... 607/36 |
| 2006/0106428 | A1* | 5/2006 | Libbus et al. ................... 607/23 |
| 2006/0259092 | A1* | 11/2006 | Spadgenske et al. ........... 607/37 |
| 2008/0063490 | A1* | 3/2008 | Fruland et al. ................ 411/377 |
| 2008/0228237 | A1* | 9/2008 | Bange et al. .................... 607/32 |

* cited by examiner

*Primary Examiner* — William Levicky
(74) *Attorney, Agent, or Firm* — Schwegman Lundberg & Woessner, P.A.

(57) ABSTRACT

A vented set screw is used to secure a connection between an implantable medical device and an implantable lead. The vented set screw includes one or more venting channels that allow liquid and/or gas to flow out of the implantable medical device when the implantable lead is being inserted into the implantable medical device and secured during an implantation procedure. This prevents pressure from building up at the connection, thereby ensuring proper performance of sensing and/or therapy delivery functions of the implantable medical device.

19 Claims, 4 Drawing Sheets

# VENTED SET SCREW FOR IMPLANTABLE MEDICAL DEVICE

CLAIM OF PRIORITY

This application claims the benefit of priority under 35 U.S.C. §119(e) of U.S. Provisional Patent Application Ser. No. 61/255,373, filed on Oct. 27, 2009, which is herein incorporated by reference in its entirety.

TECHNICAL FIELD

This document relates generally to implantable medical devices and particularly to a vented set screw for securing a connection between an implantable medical device and an implantable lead.

BACKGROUND

Medical devices are implanted in human bodies for monitoring physiological conditions, diagnosing diseases, treating diseases, or restoring functions of organs or tissues. Examples of such implantable medical devices include cardiac rhythm management (CRM) devices such as pacemakers and cardioverter/defibrillators, neural stimulators, neuromuscular stimulators, drug delivery devices, and biological therapy devices. In various applications, due to anatomical and/or other practical considerations, an implantable medical device may be placed in a location within a patient's body that is remote from a target region for sensing a signal and/or delivering a therapy. Therefore, an implantable lead may be used to couple the implantable medical device to the target region. For example, an implantable pacemaker may be implanted subcutaneously in the pectoral area and electrically coupled to the heart via one or more implantable leads. The one or more implantable leads and the implantable pacemaker may be connected after they have been at least partially placed in the body during the implantation procedure performed by a physician. To ensure proper delivery of therapy, there is a need to provide a reliable connection between the implantable medical device and each implantable lead.

SUMMARY

A vented set screw is used to secure a connection between an implantable medical device and an implantable lead. The vented set screw includes one or more venting channels that allow liquid and/or gas to flow out of the implantable medical device when the implantable lead is being inserted into the implantable medical device and secured during an implantation procedure. This prevents pressure from building up at the connection, thereby ensuring proper performance of sensing and/or therapy delivery functions of the implantable medical device.

In one embodiment, a set screw for securing a connection between an implantable medical device and an implantable lead includes a head including a top surface, a tip including a tip surface, a shank coupled between the head and the tip and including a threaded portion, a lateral surface coupled between the top surface and the tip surface, an axial cavity, and one or more venting channels. The axial cavity includes a portion shaped to receive a tool for rotationally moving the set screw. A cavity surface, which is coupled to the top surface, defines a shape of the axial cavity. The one or more venting channels each have a first opening on the lateral surface and an opposite second end on the cavity surface.

In one embodiment, an implantable medical device is configured to be connected to one or more implantable leads each including one or more electrodes. The implantable medical device includes electronic circuitry, a hermetically sealed housing encapsulating the electronic circuitry, and a header attached to the housing. The header includes a header bore, a screw bore, a vented set screw, and a seal plug. The header bore is configured to receive an implantable lead. The screw bore is in fluid communication with the header bore. The vented set screw is placed in the screw bore and includes an axial cavity including a portion shaped to receive a tool. The seal plug is placed at least partially in the screw bore and in contact with the vented set screw. The seal plug includes a seal slit that allows for access to the vented set screw by the tool. The vented set screw includes one or more venting channels that provide for fluid communication between the axial cavity and a cavity formed between the seal plug and the vented set screw.

In one embodiment, a method for securing a connection between an implantable medical device and an implantable lead is provided. The implantable medical device includes a header bore to receive the implantable lead, a screw bore connected to the header bore, a set screw placed in the screw bore for securing the connection, and a seal plug including a slit and placed at least partially in the screw bore and in contact with the set screw. The set screw includes an axial cavity for receiving a tool through the slit of the seal plug. The set screw is provided with one or more venting channels each allowing for fluid communicating between the axial cavity and a cavity formed between at least the set screw and the seal plug. When the vented set screw is being tightened, fluid in the header bore is vented through a space between the vented set screw and the screw bore, the cavity formed between at least the set screw and the seal plug, the one or more venting channels, the axial cavity of the vented set screw, and the slit of the seal plug.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a connection mechanism between an implantable medical device and an implantable lead that uses a vented set screw. When the implantable lead is inserted into the implantable medical device during an implantation procedure, liquid and/or gas may build up in one or more cavities of the connection mechanism. Without a venting channel, this buildup of liquid and/or gas results in a pressure that may push the implantable lead back out of the connection mechanism prior to being locked in place using a screw. The vented set screw includes one or more venting channels to allow the liquid and/or gas to flow out of the implantable medical device, thereby preventing excessive pressure from being built up in the connection mechanism and ensuring that the implantable lead is properly locked in place. Thus, the vented set screw provides for a secure and reliable connection between the implantable medical device and the implantable lead.

Figure 1:
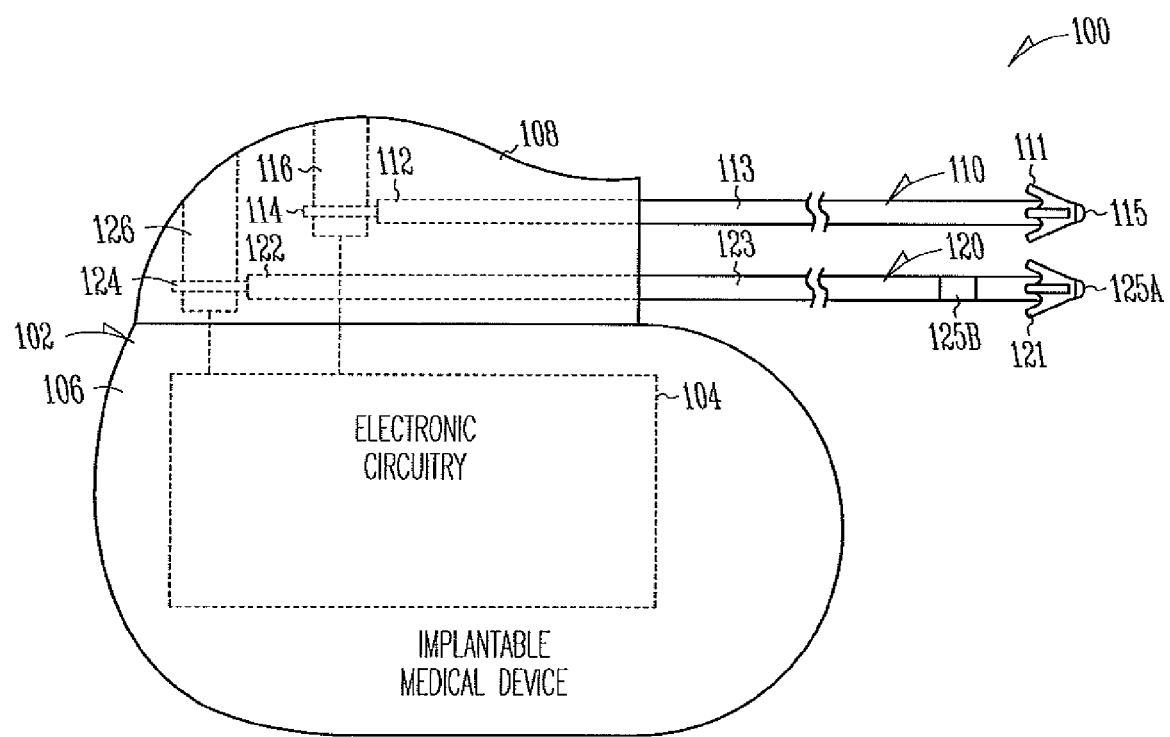
FIG. 1 is an illustration of an embodiment of an implantable system.

FIG. 1 is an illustration of an embodiment of an implantable system 100 that includes an implantable medical device 102 connected to implantable leads 110 and 120. The configuration of system 100 as shown in FIG. 1 is for illustrating purposes only, to show where vented set screws are used according to the present subject matter. In various embodiments, system 100 may include an implantable medical device of any shape and connected to any number of implantable leads. In various embodiments, system 100 is to be implanted within a patient's body for chronic use such as monitoring physiological conditions of the patient and delivering therapies to the patient. In various embodiments, implantable medical device 102 includes one or more of a physiological function monitor, a pacemaker, a cardioverter defibrillator, a neurostimulator, a drug delivery device, a biological therapy device, or a combination of any two or more of such devices.

In various embodiments, implantable medical device 102 includes electronic circuitry 104 that performs monitoring and/or therapeutic functions. The monitoring functions includes, for example, sensing one or more physiological signals such as electrocardiograms and neural traffic. Such one or more physiological signals provide for monitoring of the patient conditions. The therapeutic functions includes, for example, delivering one or more of cardiac pacing therapy, cardioversion/defibrillation therapy, neurostimulation therapy, drug therapy, and biologic therapy. Implantable medical device 102 includes a hermetically sealed housing 106 that encapsulates electronic circuitry 104. In various embodiments, housing 106 includes a can made of a biocompatible metal such as titanium. Implantable medical device 102 also includes a header 108 attached to housing 106. Header 108 includes a connection mechanism 116 and a connection mechanism 126. Connection mechanism 116 provides for a connection between implantable medical device 102 and implantable lead 110. Connection mechanism 126 provides for a connection between implantable medical device 102 and implantable lead 120. In various embodiments, connection mechanisms 116 and 126 are identical or substantially similar, and each include a venting mechanism to prevent pressure build up as implantable lead 110/120 is being connected and secured to implantable medical device 102, as further discussed below with reference to FIGS. 2-8.

In the illustrated embodiment, implantable lead 110 includes a distal end 111, a proximal end 112, and an elongate body 113 coupled between distal end 111 and proximal end 112. Distal end 111 includes an electrode 115 for sensing a signal and/or delivering an electrical therapy. Proximal end 112 is to be inserted into implantable medical device 102 and includes a terminal pin 114. Implantable lead 120 includes a distal end 121, a proximal end 122, and an elongate body 123 coupled between distal end 121 and proximal end 122. Distal end 121 includes electrodes 125A-B for sensing a signal and/or delivering an electrical therapy. Proximal end 122 is to be inserted into implantable medical device 102 and includes a terminal pin 124. In various embodiments, implantable medical device 102 is connected to one or more implantable leads similar to leads 110 and 120 and each including one or more electrodes electrically coupled to electronic circuitry 104.

Figure 2:
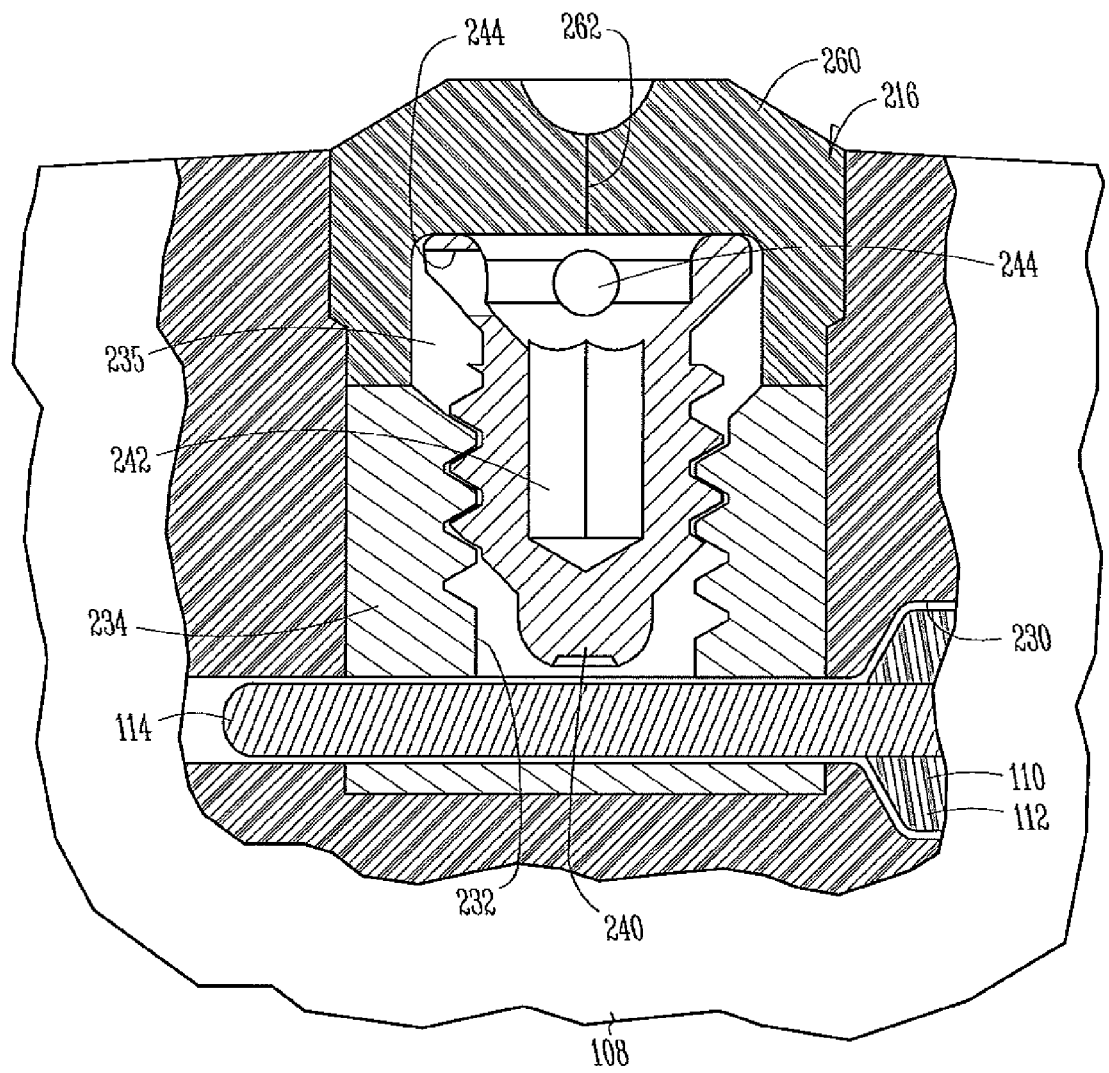
FIG. 2 is a cutaway view illustrating an embodiment of a connection mechanism between an implantable medical device and an implantable lead.

FIG. 2 is a cutaway view illustrating an embodiment of a connection mechanism 216 between implantable medical device 102 and implantable lead 110. Connection mechanism 216 represents an embodiment of connection mechanism 116 and connection mechanism 126.

Header 108 of implantable medical device 102 includes a header bore 230 and a screw bore 232. Header bore 230 is configured to receive proximal end 112 of implantable lead 110. Screw bore 232 is connected to header bore 230 and in fluid communication with header bore 232. A conductive contact 234 forms a portion of screw bore 232 and a portion of header bore 230. Conductive contact 234 is electrically connected to electronic circuitry 104 and is electrically connected to terminal pin 114 when lead 110 is inserted into implantable medical device 102. Terminal pin 114 is electrically connected to electrode 115 through a conductor extending within elongate body 113. Screw bore 232 is perpendicular to header bore 230 and includes a threaded surface to receive a set screw.

A vented set screw 240 is placed in screw bore 232. Vented set screw 240 has an axial cavity 242 including a portion shaped to receive a tool. An example of the tool includes a wrench for rotationally moving vented set screw 240. A seal plug 260 is placed at least partially in screw bore 232, over vented set screw 240. Seal plug 260 is in contact with vented set screw 240, thus forming a cavity 235 between seal plug 260 and vented set screw 240. Seal plug 260 is made of an elastic material and includes a seal slit 262 allowing for access to vented set screw 240 by the tool. In the illustrated embodiment, vented set screw 240 includes venting channels 244 that provides for fluid communication between axial cavity 242 and cavity 235. In various other embodiments, vented set screw 240 includes any number of one or more venting channels 244 each positioned in fluid communication with header bore 230, screw bore 232, and/or cavity 235.

During insertion of implantable lead 110 into header bore 230, liquid and/or gas are compressed into header bore 230 by distal end 112 of implantable lead 110, which seals header bore 230. Without pressure relief, when implantable lead 110 is released prior to being secured in header bore 232 by tightening a set screw (similar to vented set screw 240 but without venting channels 244), it can be partially ejected from header bore 230 and become improperly connected to implantable medical device 102. The improper connection may include a poor electrical connection, or no electrical connection at all, between implantable lead 110 and implantable medical device 102, thereby preventing system 100 from functioning as intended.

When implantable medical device 102 is being manufactured, the set screw is placed in screw bore 232, which is then sealed with seal plug 260 that may be in intimate contact with the set screw. Thus, while the liquid and/or gas may flow between the lateral (threaded) surface of the set screw and screw bore 232 before the set screw is tightened, the liquid and/or gas are trapped in cavity 235 (without venting channels 244). Insertion of the tool such as the wrench through seal slit 262 may not create a space allowing the liquid and/or gas to flow out of cavity 235 through the contact between seal plug 260 and set screw 240 and then seal slit 262.

Venting channels 244 allow for the liquid and/or gas to flow from cavity 235 to axial cavity 242 and then flow out of seal plug 260 through seal slit 262 while the tool such as the wrench is inserted. After the wrench is removed, if enough pressure has built up by the liquid and/or gas in axial cavity 242, a portion of the liquid and/or gas will burp out of seal plug 260 through seal slit 262.

In various embodiments, an implantable medical device may include one or more header bores to receive one or more implantable leads, one or more screw bores each connected to a header bore of the one or more header bores, and one or more vented set screws each placed in a screw bore of the one or more screw bores. In other words, the implantable medical device may include any number of one or more connection mechanisms each being similar to connection mechanism 216.

Figures 3, 4:
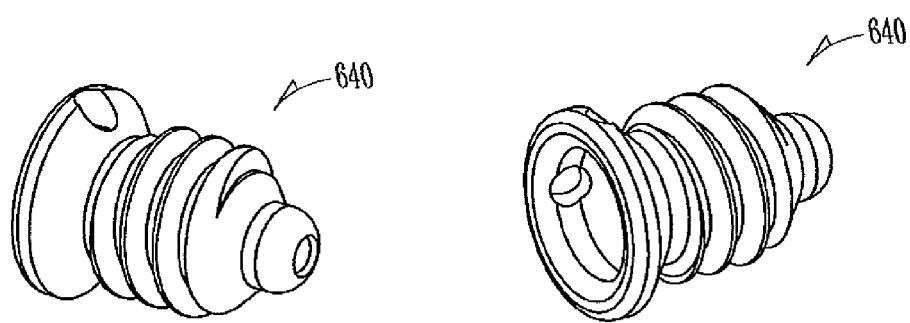
FIG. 3 is an isometric view illustrating an embodiment of a vented set screw.
FIG. 4 is another isometric view illustrating the vented set screw of FIG. 3.
Figure 5:
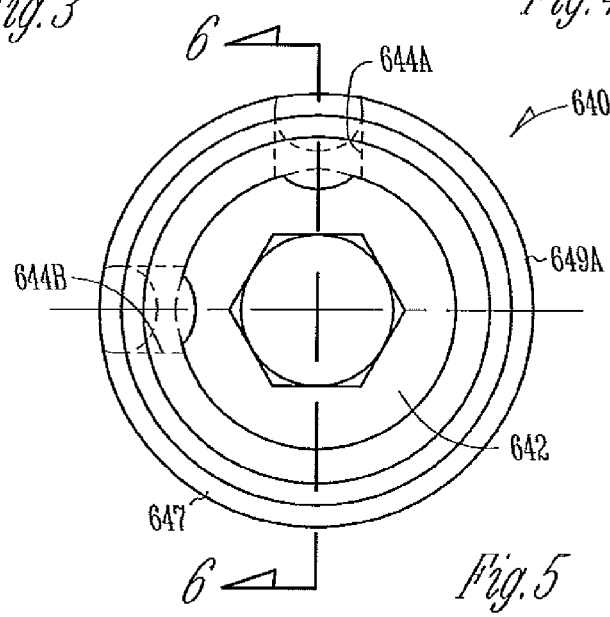
FIG. 5 is a top-view illustrating the vented set screw of FIG. 3.
Figure 6:
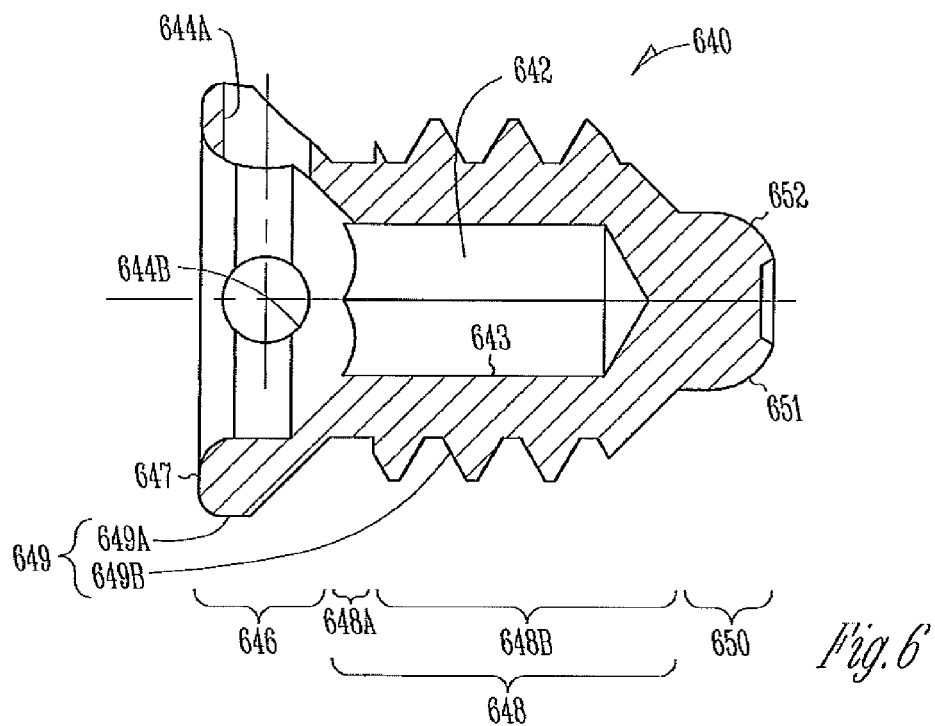
FIG. 6 is a side-view illustrating the vented set screw of FIG. 3.

FIGS. 3-6 illustrate an embodiment of a vented set screw 640, which represents an embodiment of vented set screw 240. FIGS. 3 and 4 are isometric views illustrating vented set screw 640 from different angles. FIG. 5 is a top-view illustrating vented set screw 640, and FIG. 6 is a side-view illustrating vented set screw 640.

Vented set screw 640 includes a head 646, a tip 650, and a shank 648 coupled between head 646 and tip 650. In the illustrated embodiment, shank 648 has a threaded portion 648B coupled to tip 650 and a thread relief portion 648A coupled to head 646. Head 646 includes a top surface 647, which may be in contact with seal plug 260 when placed in screw bore 232. Tip 650 includes a tip surface 651 that defines the shape of tip 650. Top surface 647 and tip surface 651 are on opposite axial ends of vented set screw 640. In various embodiments, tip 650 may have different shapes to fit into screw bore 232 and allow for proper contact with terminal pin 114.

Vented set screw 640 has a lateral surface 649 that is generally co-axial with the longitudinal axis of vented set screw 640 and is coupled between top surface 647 and tip surface 651. Lateral surface 649 includes a head portion 649A and a shank portion 649B. Head portion 649A is a surface of head 646 and coupled to top surface 647. Shank portion 649B is a surface of shank 648 and coupled between head surface portion 649A and tip surface 651.

Vented set screw 640 includes an axial cavity 642, which includes a portion shaped to receive a tool for rotationally moving vented set screw 640. Axial cavity 640 is within head 646 and shank 648 and has a cavity surface 643 that is coupled to top surface 647 and defines the shape of axial cavity 642. In the illustrated embodiment, a portion of axial cavity 642 has a hexagonal cross-section to receive a wrench having a hexagonal head. Head 646, shank 648, tip 650, and axial cavity 642 are approximately coaxially aligned. The overall surface of vented set screw 640 includes top surface 647, tip surface 652, lateral surface 649, and cavity surface 643.

In the illustrated embodiment, vented set screw 640 includes venting channels 644A-B that allow for fluid communication between axial cavity 642 and cavity 235. Venting channels 644A-B each have a first opening on lateral wall 649 and an opposite second opening on cavity wall 643. In the illustrated embodiment, venting channels 644A-B are in head 646 and are each a hole having a first opening on head portion 649A of lateral surface 649 and an opposite second end on cavity surface 643. The hole has a cross-section having a shape and size determined based on considerations on mechanical properties of vented set screw 640 and ease of manufacturing. In the illustrated embodiment, the hole has an approximately circular cross-section.

Figure 7:
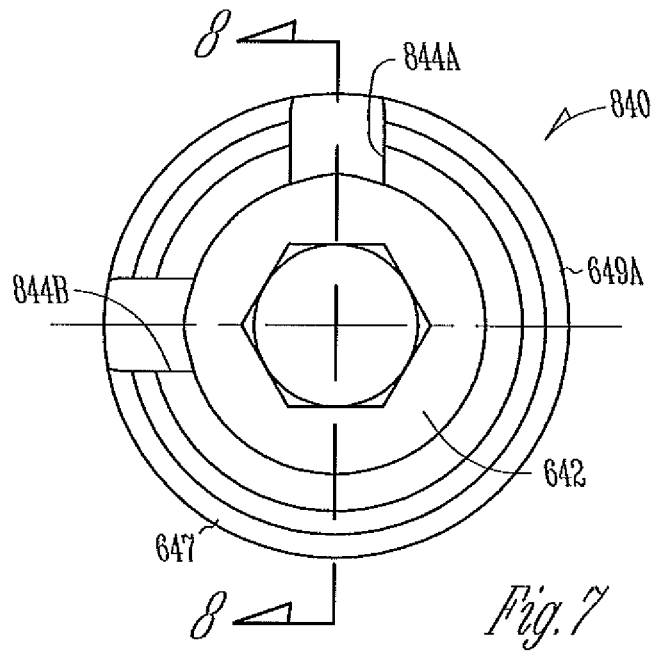
FIG. 7 is a top-view illustrating another embodiment of a vented set screw.
Figure 8:
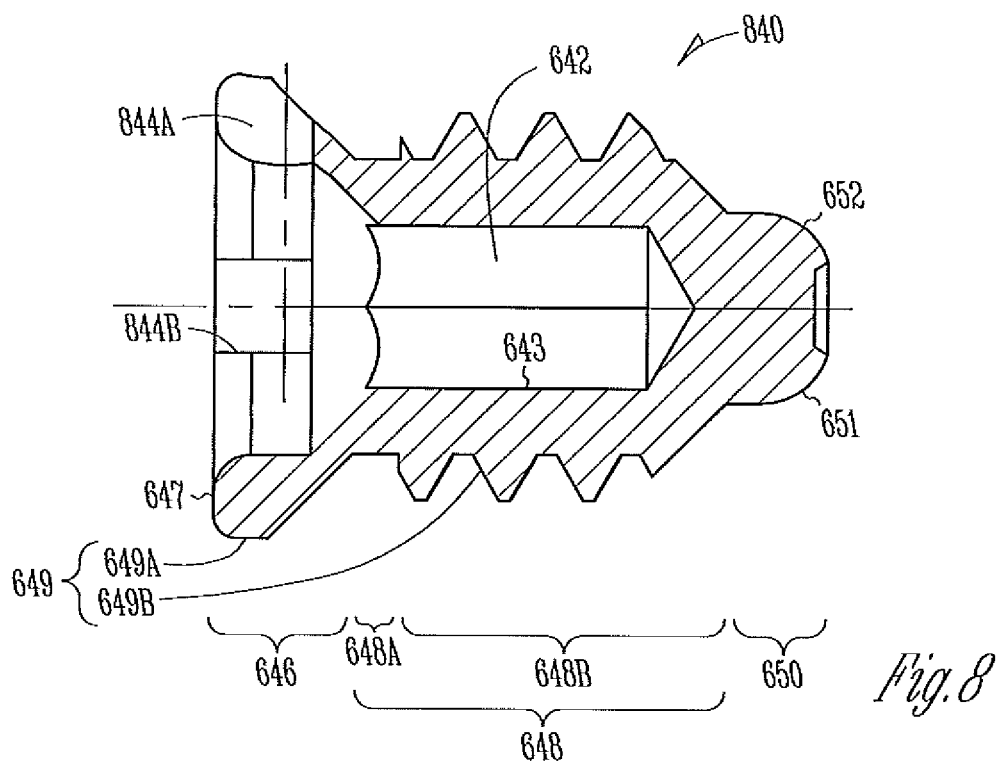
FIG. 8 is a side-view illustrating the vented set screw of FIG. 7.

FIGS. 7 and 8 illustrate an embodiment of a vented set screw 840, which represents another embodiment of vented set screw 240. FIG. 7 is a top-view illustrating vented set screw 840, and FIG. 8 is a side-view illustrating vented set screw 840.

In the illustrated embodiment, vented set screw 840 is substantially similar to vented set screw 640 except that vented set screw 840 includes venting channels 844A-B that are each a slot on lop surface 647. The slot has a first end on lateral surface 649 and an opposite second end on cavity surface 643. The slot has a cross-section having a shape and size determined based on considerations on mechanical properties of vented set screw 840 and ease of manufacturing.

Vented set screw 240 is made of a biocompatible material such as titanium or stainless steel. In various embodiments, the vented set screw according to the present subject matter is manufactured using the same machining process used to made set screws without the one or more venting channels, with an addition step of forming the one or more venting channels such as the one or more holes or slots. There is no need to modify the procedure of implanting the system by the physician because the vented set screw is tightened to secure the connection between an implantable medical device and an implantable lead using the same type tool in the same way as tightening an unvented set screw.

It is to be understood that the above detailed description is intended to be illustrative, and not restrictive. For example, a vented set screw according to the present subject matter may include any number of one or more venting channels each having any suitable cross-sectional shape and located to provide a desirable path of fluid communication for pressure relief. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device configured to be connected to one or more implantable leads each including one or more electrodes, the implantable medical device comprising:
   electronic circuitry;

a hermetically sealed housing encapsulating the electronic circuitry; and
a header attached to the housing, the header including:
a header bore configured to receive an implantable lead of the one or more implantable leads;
a screw bore in fluid communication with the header bore;
a vented set screw placed in the screw bore, the vented set screw including an axial cavity including a portion shaped to receive a tool; and
a seal plug placed at least partially in the screw bore and in contact with the vented set screw, the seal plug including a seal slit allowing for access to the vented set screw by the tool,
wherein the vented set screw includes one or more venting channels providing for fluid communication between the axial cavity and a cavity formed between the seal plug and the vented set screw, the one or more venting channels each being a hole having an approximately circular cross-section.

2. The implantable medical device of claim 1, wherein the electronic circuitry is adapted to sense one or more physiological signals.

3. The implantable medical device of claim 2, wherein the electronic circuitry is adapted to deliver one or more of cardiac pacing and cardioversion/defibrillation.

4. The implantable medical device of claim 2, wherein the electronic circuitry is adapted to deliver neurostimulation.

5. The implantable medical device of claim 2, wherein the electronic circuitry is adapted to sense electrocardiograms.

6. The implantable medical device of claim 2, wherein the electronic circuitry is adapted to sense neural traffic.

7. The implantable medical device of claim 1, wherein the screw bore is approximately perpendicular to the header bore.

8. The implantable medical device of claim 1, wherein the vented set screw comprises:
a head including a top surface;
a tip including a tip surface;
a shank coupled between the head and the tip and including a threaded portion; and
a lateral surface coupled between the top surface and the tip surface,
and wherein the axial cavity is within the head and the shank and has a cavity surface coupled to the top surface and defining a shape of the axial cavity.

9. The implantable medical device of claim 8, wherein the head, the shank, the tip portion, and the axial cavity are approximately coaxially aligned.

10. The implantable medical device of claim 9, wherein the one or more venting channels are in the head.

11. The implantable medical device of claim 8, wherein the hole has a first opening on the lateral surface and an opposite second opening on the cavity surface.

12. The implantable medical device of claim 8, wherein the shank further comprises a thread relief portion coupled to the head.

13. The implantable medical device of claim 1, wherein the header comprises a plurality of the header bores configured to receive a plurality of implantable leads of the one or more implantable leads, a plurality of the screw bores each in communication with a header bore of the plurality of the header bores, a plurality of the vented set screws each placed in a screw bore of the plurality of the screw bores, and a plurality of the seal plugs each placed at least partially in a screw bore of the plurality of the screw bores and in contact with the vented set screw in that screw bore.

14. The implantable medical device of claim 1, wherein the vented set screw is made of titanium.

15. The implantable medical device of claim 1, wherein the vented set screw is made of stainless steel.

16. The implantable medical device of claim 1, wherein the axial cavity has a hexagonal cross-section.

17. The implantable medical device of claim 1, wherein the electronic circuitry is adapted to perform therapeutic functions.

18. The implantable medical device of claim 1, wherein the electronic circuitry is adapted to deliver a drug therapy.

19. The implantable medical device of claim 1, wherein the electronic circuitry is adapted to deliver a biologic therapy.

* * * * *